(12) United States Patent  (10) Patent No.: US 8,118,827 B2
Duerig et al.  (45) Date of Patent: Feb. 21, 2012

(54) TOTAL OCCLUSION GUIDEWIRE DEVICE

(75) Inventors: Thomas W. Duerig, Fremont, CA (US); Hikmat Hojeibane, Princeton, NJ (US); David C. Majercak, Stewartsville, NJ (US)

(73) Assignee: Cordis Corporation, Bridgewater, NJ (US)

( * ) Notice: Subject to any disclaimer, the term of this patent is extended or adjusted under 35 U.S.C. 154(b) by 1171 days.

(21) Appl. No.: 10/388,699

(22) Filed: Mar. 14, 2003

(65) Prior Publication Data

US 2003/0139763 A1    Jul. 24, 2003

Related U.S. Application Data

(62) Division of application No. 09/800,351, filed on Mar. 6, 2001, now Pat. No. 6,579,302.

(51) Int. Cl.
*A61M 29/00* (2006.01)
(52) U.S. Cl. ......................................... 606/198; 604/107
(58) Field of Classification Search ................... 606/127, 606/198, 200, 159, 114, 128; 600/434, 585; 604/104–107
See application file for complete search history.

(56) References Cited

U.S. PATENT DOCUMENTS

| | | | |
|---|---|---|---|
| 3,789,841 A | 2/1974 | Antoshkiw | |
| 4,545,390 A | 10/1985 | Leary | |
| 4,573,966 A | 3/1986 | Weikl | |
| 4,590,938 A * | 5/1986 | Segura et al. | 606/127 |
| 4,619,274 A | 10/1986 | Morrison | |
| 4,665,905 A | 5/1987 | Brown | |
| 4,807,626 A * | 2/1989 | McGirr | 606/127 |
| 4,921,484 A * | 5/1990 | Hillstead | 604/104 |
| 4,925,445 A | 5/1990 | Sakamoto et al. | |
| 4,926,858 A | 5/1990 | Brown | |
| 4,969,890 A | 11/1990 | Sugita et al. | |
| 4,984,581 A | 1/1991 | Stice | |
| 4,988,356 A | 1/1991 | Crittenden et al. | |
| 4,991,602 A | 2/1991 | Amplatz et al. | |
| 5,069,226 A | 12/1991 | Yamauchi et al. | |
| 5,095,915 A | 3/1992 | Engelson | |
| 5,108,419 A | 4/1992 | Reger et al. | |
| 5,171,383 A | 12/1992 | Sagae et al. | |
| 5,303,714 A | 4/1994 | Abele et al. | 600/585 |
| 5,345,937 A | 9/1994 | Middleman et al. | |
| 5,364,718 A | 11/1994 | Oae et al. | |
| 5,395,383 A * | 3/1995 | Adams et al. | 606/151 |
| 5,497,782 A | 3/1996 | Fugoso | 600/585 |
| 5,512,044 A | 4/1996 | Duer | |
| 5,628,751 A | 5/1997 | Rizik | |

(Continued)

FOREIGN PATENT DOCUMENTS

DE    197 22 429 A1    12/1998

(Continued)

OTHER PUBLICATIONS

European Search Report EP 05077768 dated Jan. 31, 2006.

(Continued)

*Primary Examiner* — Victor Nguyen
(74) *Attorney, Agent, or Firm* — Carl J. Evens

(57) ABSTRACT

A guidewire having a spreader or at least one centering device which may be used to open occluded vessels or other biological passages, especially chronic total occlusions. The guidewire may be used to either open the lumen or to center a boring device within the lumen, so that the chronic total occlusion can be crossed, and an interventional procedure can then be performed.

5 Claims, 4 Drawing Sheets

U.S. PATENT DOCUMENTS

| | | | |
|---|---|---|---|
| 5,628,761 A | 5/1997 | Rizik | 606/170 |
| 5,653,684 A | 8/1997 | Yurek | |
| 5,713,907 A | 2/1998 | Hogendijk | |
| 5,769,816 A * | 6/1998 | Barbut et al. | 604/93.01 |
| 5,792,157 A * | 8/1998 | Mische et al. | 606/159 |
| 5,814,064 A | 9/1998 | Daniel et al. | |
| 5,830,156 A | 11/1998 | Ali et al. | 600/585 |
| 5,916,235 A | 6/1999 | Guglielmi | |
| 5,921,958 A | 7/1999 | Ressemann et al. | |
| 5,941,896 A | 8/1999 | Kerr | |
| 5,972,019 A | 10/1999 | Engelson et al. | |
| 6,059,814 A | 5/2000 | Ladd | |
| 6,146,396 A * | 11/2000 | Konya et al. | 606/159 |
| 6,336,934 B1 * | 1/2002 | Gilson et al. | 606/200 |
| 6,355,051 B1 | 3/2002 | Sisskind et al. | |
| 6,485,458 B1 | 11/2002 | Takahashi | |
| 6,579,302 B2 | 6/2003 | Duerig et al. | |
| 7,691,123 B2 | 4/2010 | Tsugita et al. | |
| 7,776,083 B2 | 8/2010 | Vesely | |

FOREIGN PATENT DOCUMENTS

| | | |
|---|---|---|
| EP | 0 418 677 A1 | 3/1991 |
| EP | 0 657 140 A1 | 6/1995 |
| EP | 0 289 319 A2 | 11/1998 |
| WO | 99/22673 A1 | 5/1999 |
| WO | WO 00/13738 A | 3/2000 |

OTHER PUBLICATIONS

European Search Report EP 05077767 dated Feb. 15, 2006.

European Search Report EP 05077766.3 dated Mar. 30, 2006.

* cited by examiner

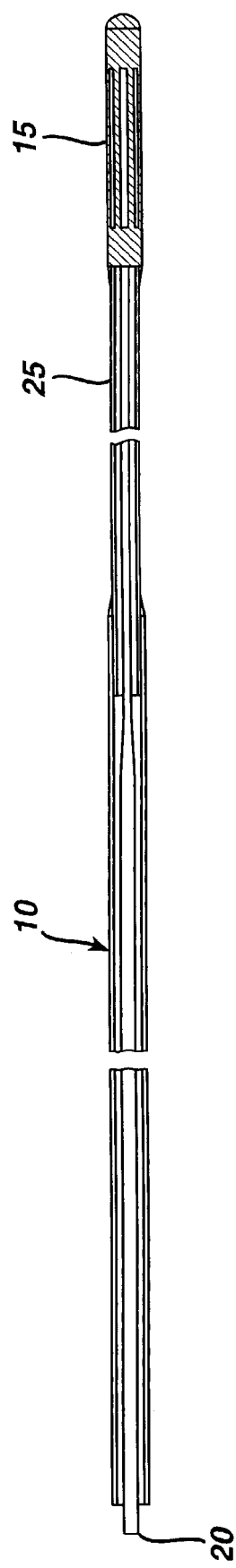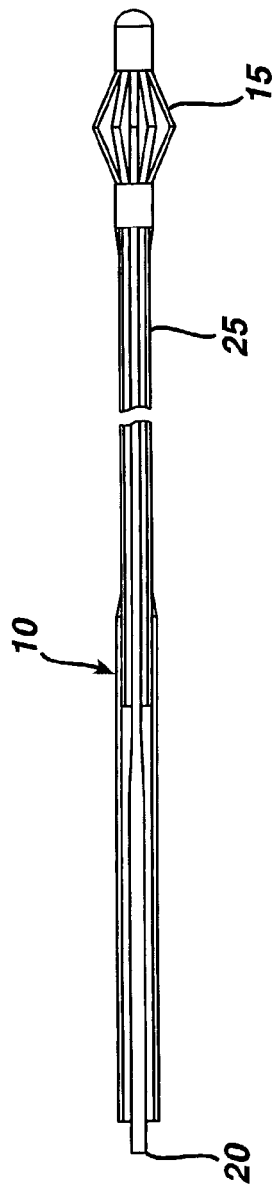

TOTAL OCCLUSION GUIDEWIRE DEVICE

This application is a divisional application of U.S. application Ser. No. 09/800,351 filed Mar. 6, 2001, now U.S. Pat. No. 6,579,302, the contents of which are hereby incorporated herein by reference.

BACKGROUND OF THE INVENTION

1. Field of the Invention

The present invention relates to a guidewire, and more particularly to a guidewire which can cross a vessel which is totally occluded.

2. Discussion of Related Art

Percutaneous transluminal coronary angioplasty (PTCA) and stenting are therapeutic medical procedures used to increase blood flow through the coronary arteries and can often be used as alternatives to coronary bypass surgery. In PTCA procedures, the angioplasty balloon is inflated within the stenosed vessel, at the location of an atheroma or plaque deposit, in order to shear and disrupt the wall components of the vessel to obtain an enlarged lumen. In stenting, an endoluminal prosthesis is implanted in the vessel to maintain patency following the procedure. In order to initiate these procedures, one must first introduce a guidewire into the lumen of the vessel to serve as a conduit for other interventional devices, such as angioplasty balloons and stent delivery systems. This guidewire must be advanced into a position past the location of the atheroma or plaque deposit.

Guidewires should be capable of traversing tortuous pathways within the body, consisting of bends, loops and branches. For this reason, guidewires need to be flexible, but they should also be sufficiently stiff to serve as a conduit for other devices. In addition, they must be torqueable to facilitate directional changes as they are guided into position. Guidewires are typically made of stainless steel, tantalum or other suitable materials, and include a variety of different designs. For example, U.S. Pat. Nos. 3,789,841, 4,545,390 and 4,619,274 disclose guidewires in which the distal segment is tapered for greater flexibility. The tapered section may be enclosed in a wire coil, typically a platinum coil, which provides increased column strength and torqueability. Another design is identified in U.S. Pat. No. 5,095,915, where the distal segment is encased in a polymer sleeve with axially spaced grooves to provide bending flexibility.

In some cases, a vessel may be totally occluded, and even a guidewire cannot be introduced. This condition is referred to as a chronic total occlusion. In these cases, the true lumen of the vessel is embedded in the occlusion and is surrounded by false lumens that have been created over time. As the clinician attempts to cross the true lumen, the tip of the guidewire tends to penetrate the false lumens of the occlusion, which may result in vessel perforation, dissection, or release of plaque particles into the bloodstream. Also, as the clinician attempts to cross the lumen, the tip of the guidewire has a natural tendency to be directed toward the side of the occlusion rather than the center due to the configuration of the occlusion, which can also result in vessel perforation, dissection and inability to cross the occlusion. There is currently no effective interventional treatment method for such cases.

The prior art makes reference to the use of alloys such as Nitinol (Ni—Ti alloy), which have shape memory and/or superelastic characteristics, in medical devices which are designed to be inserted into a patient's body. The shape memory characteristics allow the devices to be deformed to facilitate their insertion into a body lumen or cavity, and then heated within the body so that the device returns to its original shape. Superelastic characteristics, on the other hand, generally allow the metal to be deformed and restrained in the deformed condition to facilitate the insertion of the medical device containing the metal into a patient's body, with such deformation causing the phase transformation. Once within the body lumen, the restraint on the superelastic member can be removed, thereby reducing the stress therein so that the superelastic member can return to its original un-deformed shape by the transformation back to the original phase.

Alloys having shape memory/superelastic characteristics generally have at least two phases. These phases are a martensite phase, which has a relatively low tensile strength and which is stable at relatively low temperatures, and an austenite phase, which has a relatively high tensile strength and which is stable at temperatures higher than the martensite phase.

Shape memory characteristics are imparted to the alloy by heating the metal to a temperature above which the transformation from the martensite phase to the austenite phase is complete, i.e. a temperature above which the austenite phase is stable (the Af temperature). The shape of the metal during this heat treatment is the shape "remembered." The heat-treated metal is cooled to a temperature at which the martensite phase is stable, causing the austenite phase to transform to the martensite phase. The metal in the martensite phase is then plastically deformed, e.g. to facilitate the entry thereof into a patient's body. Subsequent heating of the deformed martensite phase to a temperature above the martensite to austenite transformation temperature causes the deformed martensite phase to transform to the austenite phase and during this phase transformation the metal reverts back to its original shape if unrestrained. If restrained, the metal will remain martensitic until the restraint is removed.

Methods of using the shape memory characteristics of these alloys in medical devices intended to be placed within a patient's body present operational difficulties. For example, with shape memory alloys having a stable martensite temperature below body temperature, it is frequently difficult to maintain the temperature of the medical device containing such an alloy sufficiently below body temperature to prevent the transformation of the martensite phase to the austenite phase when the device was being inserted into a patient's body. With intravascular devices formed of shape memory alloys having martensite-to-austenite transformation temperatures well above body temperature, the devices can be introduced into a patient's body with little or no problem, but they are typically heated to the martensite-to-austenite transformation temperature which is frequently high enough to cause potential tissue damage and patient discomfort.

When stress is applied to a specimen of a metal, such as Nitinol, exhibiting superelastic characteristics at a temperature above which the austenite is stable (i.e. the temperature at which the transformation of martensite phase to the austenite phase is complete), the specimen deforms elastically until it reaches a particular stress level where the alloy then undergoes a stress-induced phase transformation from the austenite phase to the martensite phase. As the phase transformation proceeds, the alloy undergoes significant increases in strain but with little or no corresponding increases in stress. The strain increases while the stress remains essentially constant until the transformation of the austenite phase to the martensite phase is complete. Thereafter, further increases in stress are necessary to cause further deformation. The martensitic metal first deforms elastically upon the application of additional stress and then plastically with permanent residual deformation.

If the load on the specimen is removed before any permanent deformation has occurred, the martensitic specimen will elastically recover and transform back to the austenite phase. The reduction in stress first causes a decrease in strain. As stress reduction reaches the level at which the martensite phase transforms back into the austenite phase, the stress level in the specimen will remain essentially constant (but substantially less than the constant stress level at which the austenite transforms to the martensite) until the transformation back to the austenite phase is complete, i.e. there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as superelasticity or pseudoelasticity. It is this property of the material which makes it useful in manufacturing tube-cut self-expanding stents. The prior art makes reference to the use of metal alloys having superelastic characteristics in medical devices which are intended to be inserted or otherwise used within a patient's body. See for example, U.S. Pat. No. 4,665, 905 (Jervis).

Some guidewire designs have recommended the use of superelastic alloys. For example, U.S. Pat. No. 4,925,445 discloses a guidewire where the distal segment, and at least one portion of the proximal segment, is made from a superelastic alloy like Nitinol, where the transformation temperature from austenite to martensite occurs at 10° C. or below. Also, U.S. Pat. No. 4,984,581 discloses a guidewire having a core of shape memory alloy, where the shape memory properties of the alloy provide both tip-deflection and rotational movement in response to a controlled themal stimulus. Other guidewires made from superelastic Nitinol alloys include U.S. Pat. Nos. 4,969,890, 4,991,602, 5,069,226, and 5,171, 383.

However, the prior art has yet to disclose any guidewires made from self-expanding, shape-memory alloys which may be used to address the clinical problem of chronic total occlusions.

SUMMARY OF THE INVENTION

The present invention provides for a guidewire which may be used to cross chronic total occlusions, and which overcomes many of the disadvantages associated with the prior art devices, as briefly described above.

In accordance with one aspect, the present invention is directed to a guidewire comprising a flexible wire having an outer diameter and an inner diameter, a spreader attached to the distal end of the flexible wire, having a smaller first diameter for insertion into a vessel, and a larger second diameter for expanding the lumen of the vessel, and a core wire inserted into the flexible wire and the spreader, which is used to control the diameter of the spreader. The spreader is then advanced though the chronic total occlusion in a ratcheting fashion to open the vessel.

In accordance with another aspect, the present invention is directed to a guidewire comprising a flexible wire having an outer diameter and an inner diameter, a spreader attached to the distal end of the flexible wire, having a smaller first diameter for insertion into a vessel, and a larger second diameter for expanding the lumen of the vessel, and a sheath inserted over the flexible wire and the spreader, which is used to control the diameter of the spreader. The spreader is then advanced though the chronic total occlusion in a ratcheting fashion to open the vessel.

In accordance with another aspect, the present invention is directed to a guidewire comprising a flexible wire having an outer diameter and an inner diameter, at least one centering device attached to the distal end of the flexible wire, having a smaller first diameter for insertion into a vessel, and a larger second diameter for centering the device in the lumen of the vessel, and a sheath inserted into over the flexible wire and the centering device, which is used to control the diameter of the centering device. The present invention also comprises a rotatable core wire with a boring tip, which is inserted through the flexible wire and the centering device or devices, and rotated while in contact with the occlusion, to open the lumen of the vessel.

The advantages of the present invention are that the superelastic capabilities of Nitinol may be used to either open the lumen or to center a boring device within the lumen, so that the chronic total occlusion may be crossed. Once the occlusion is crossed, additional interventional devices such as angioplasty balloons and stents may be advanced over the guidewire, and may be placed at the site of the occlusion, so that balloon angioplasty, stenting, or other interventional procedures may then be performed. As a result, currently untreatable patients, whose only alternative is often bypass surgery, may be treated in a less-invasive fashion through the use of this device.

BRIEF DESCRIPTION OF DRAWINGS

The foregoing and other aspects of the present invention will best be appreciated with reference to the detailed description of the invention in conjunction with the accompanying drawings, wherein:

FIG. 1 is a simplified, partial cross-sectional view of an exemplary embodiment of the total occlusion guidewire device, with the spreader in the closed position, in accordance with the present invention.

FIG. 2 is a view similar to that of FIG. 1 but showing the spreader in the open position in accordance with the present invention.

DETAILED DESCRIPTION OF THE PREFERRED EMBODIMENTS

The total occlusion guidewire device of the present invention is designed to cross a totally occluded vessel. The device comprises various means for opening the true lumen of the vessel, including spreaders, centering devices and boring guide tips. The spreader is simply positioned in proximity to the occlusion and opened to increase the diameter of the lumen, in order to advance the guidewire through the lumen. Centering devices with boring guide tips may also be utilized to open the true lumen of the vessel. Centering devices may be utilized to position and retain a boring guide tip in the center of the lumen in order to insure proper positioning, and then the boring guide tip may be utilized to essentially cut through the occlusion if necessary.

Figure 7:
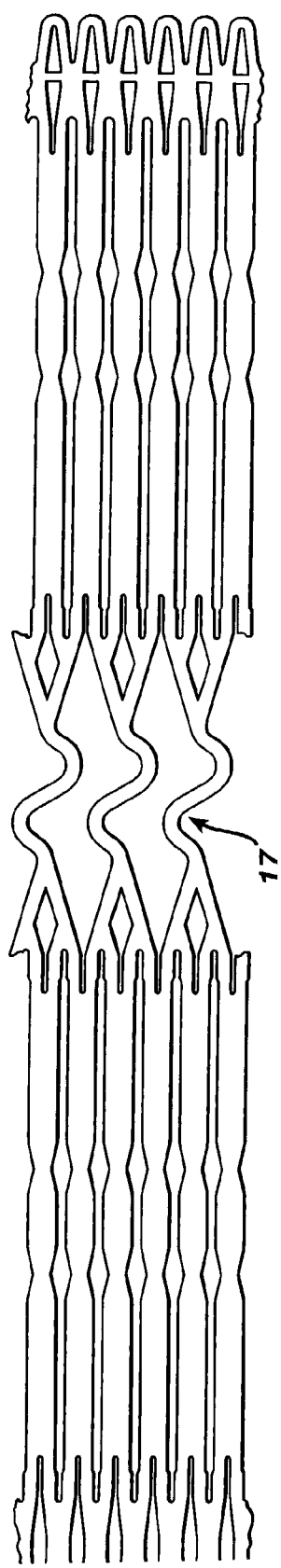
FIG. 7 is an enlarged, simplified, partial cross-sectional view of a segment of the spreader or the centering device.

While the present invention may be realized in a number of exemplary embodiments, for ease of explanation, three exemplary embodiments will be described in detail. Referring to the figures wherein like numerals indicate the same element throughout the views, there is shown in FIGS. 1 and 2, a total occlusion guidewire device 10 made in accordance with the present invention. The total occlusion guidewire device 10 comprises a flexible wire 25, a spreader 15, which is permanently or removably attached to the distal end of the flexible wire 25, and a core wire 20, which is used to control the diameter of the spreader. As illustrated in FIG. 1, the core wire 20 has been inserted into the flexible wire 25 and slidably advanced through the flexible wire 25 and the spreader 15, and is substantially in contact with the distal end of the spreader 15. Therefore, as illustrated in FIG. 1, the spreader 15 has achieved its longest length and its smallest diameter and is in the closed position. In FIG. 2, the slidable, core wire 20 has been advanced through the flexible wire 25 only, and is substantially in contact with the proximal end of the spreader 15, thereby causing the spreader 15 to achieve its shortest length and to open up to its largest diameter. The spreader 15 may comprise a plurality of longitudinally or circumferentially arranged struts extending between the distal portion and the proximal portion of the spreader, such that advancing the spreader 15 over the core wire 20 frees the struts and allows them to expand to their largest diameter, and advancing the core wire 20 through the spreader 15 aligns the struts in a flat, closed position. As illustrated in FIG. 7, the spreader 15 may alternately comprise a plurality of hingedly connected members 17. The core wire 20 may alternately be permanently attached to the distal end of the spreader 15. The core wire 20 may also alternately have an inner diameter to accommodate another guidewire.

Referring back to FIGS. 1 and 2, the total occlusion guidewire device 10 may be made from any number of suitable materials, and is preferably made from a superelastic alloy such as Nitinol. The core wire 20 and the flexible wire 25 may be coated with any number of lubricious, biocompatible coatings. The spreader 15 may be made from any number of suitable materials, and is preferably made from a superelastic alloy such as Nitinol.

The exemplary embodiment of the total occlusion guidewire device 10, as illustrated in FIGS. 1 and 2, is used to cross a chronic total occlusion by inserting it into the lumen of the occluded vessel, and then advancing it through the lumen until the distal end of the device is as close as possible to the occlusion. Then, the spreader 15 and the flexible wire 25 are advanced over the core wire 20, until the spreader 15 is in the open position, and achieves its shortest length and largest diameter and opens the occlusion. At this point, the core wire 20 is advanced through the flexible wire 25 and the spreader 15, until the distal end of the core wire 20 is substantially in contact with the distal end of the spreader 15, and the spreader 15 has achieved its longest length and smallest diameter and is in the closed position. This process is then repeated in a ratcheting fashion until the occlusion is fully opened. Once the occlusion is fully opened, additional interventional devices such as angioplasty balloons and stents may be advanced over the total occlusion guidewire device, and may be placed at the site of the occlusion, so that balloon angioplasty, stenting, or other interventional procedures may then be performed to complete the treatment of the patient.

Figure 3:
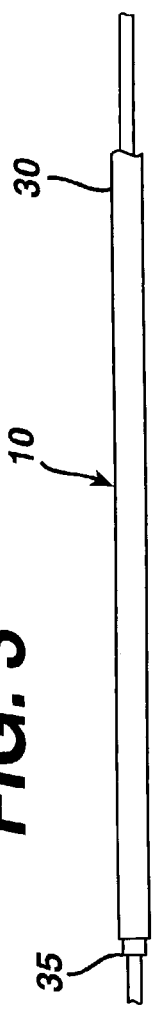
FIG. 3 is a simplified, partial cross-sectional view of another exemplary embodiment of the total occlusion guidewire device, with the sheath over the centering device in the "as delivered" position, in accordance with the present invention.
Figure 4:
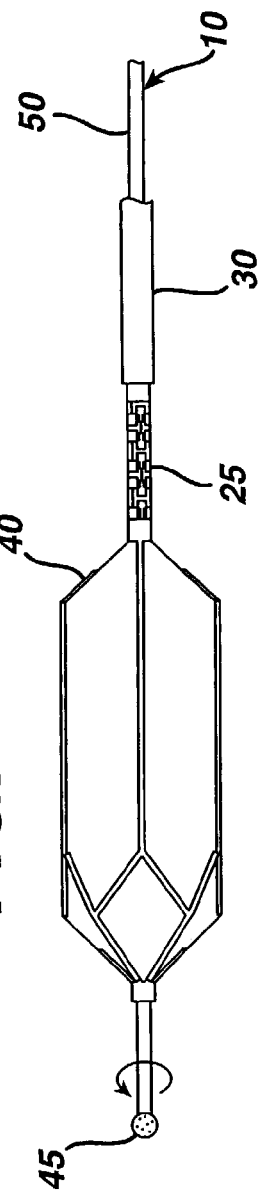
FIG. 4 is an enlarged, simplified, partial cross-sectional view similar to FIG. 3 but showing the total occlusion guidewire device with the sheath retracted, and the centering device in the "as deployed" position, in accordance with the present invention.
Figure 5:
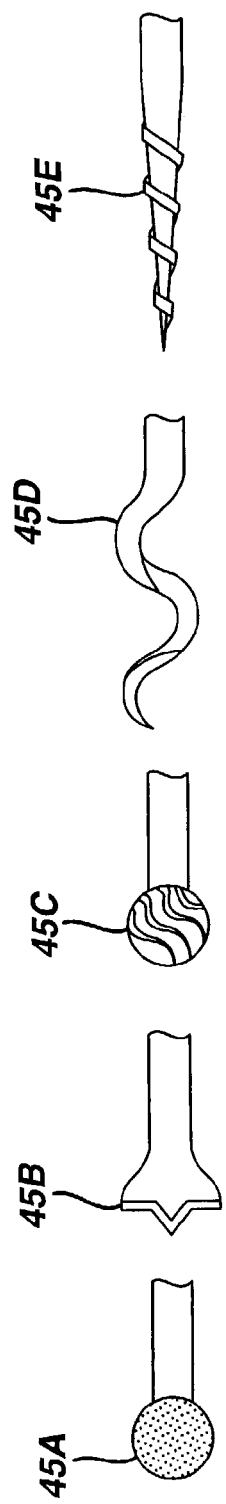
FIG. 5 is an enlarged, simplified, partial cross-sectional view of five different exemplary embodiments of the boring guide tip of the total occlusion guidewire device, in accordance with the present invention.

FIGS. 3, 4 and 5 show a second exemplary embodiment of the total occlusion guidewire device. FIG. 4 shows a total occlusion guidewire device 10, which comprises a flexible wire 25, a centering device 40, which is permanently or removably attached to the distal end of the flexible wire 25, a rotatable core wire 50, a boring guide tip 45, which is permanently or removably attached to the distal end of the rotatable core wire, and a sheath 30, which is used to control the diameter of the centering device. As illustrated in FIG. 4, the rotatable core wire 50 has been inserted into the flexible wire 25 and slidably advanced through the flexible wire 25 and the centering device 40 until the boring guide tip 45 of the rotatable core wire 50 extends beyond the distal end of the centering device 40. As illustrated in FIG. 4, the centering device 40 is in the open position and has achieved its shortest length and largest diameter. As illustrated in FIG. 3, the sheath 30 has been inserted over the flexible wire and has been slidably advanced over the flexible wire and the centering device, and is substantially in contact with the distal end of the centering device 35. Therefore, the centering device is in the closed position and has achieved its longest length and smallest diameter. The centering device 40 may comprise a plurality of longitudinal struts or circumferential struts extending between the distal portion and the proximal portion of the centering device 40, such that advancing the sheath 30 over the centering device 40 aligns the struts in a flat, closed position, and retracting the sheath 30 frees the struts and allows them to expand to their largest diameter. As illustrated in FIG. 7, the centering device may alternately comprise a plurality of hingedly connected members 17. As illustrated in FIG. 5, a number of alternate designs for the boring guide tip 45A, 45B, 45C, 45D and 45E are shown, including circular guide tips with metal oxide layers or milled ends, cutting surfaces, and screw-type configurations. As an alternate to a boring guide tip, a device providing an energy source, such as laser energy, may be utilized to penetrate the occlusion.

The total occlusion guidewire device 10 may be made from any number of suitable materials, and is preferably made from a superelastic alloy such as Nitinol. The rotatable core wire 50, the flexible wire 25, and the sheath 30 may be coated with any number of lubricious, biocompatible coatings. The centering device 40 may be made from any number of suitable materials, and is preferably made from a superelastic alloy such as Nitinol.

The exemplary embodiment of the total occlusion guidewire device 10, as illustrated in FIGS. 3, 4 and 5, is used to cross a chronic total occlusion by inserting it into the lumen of the occluded vessel, and then advancing it through the lumen until the boring guide tip 45 of the rotatable core wire 50 is as close as possible to the occlusion. Then, the sheath 30 is slidably retracted over the centering device 35 until the centering device 35 has achieved its shortest length and largest diameter, and centers the devices within the lumen of the vessel. Then, the boring guide tip 45 and the rotatable core wire 50 are slidably advanced through the flexible wire 25 until the boring guide tip 45 is substantially in contact with the occlusion. Finally, the rotatable core wire 50 and the boring guide tip 45 are rotated and advanced until the occlusion is fully opened. Once the occlusion is fully opened, additional interventional devices such as angioplasty balloons and stents may be advanced over the total occlusion guidewire device 10, and may be placed at the site of the occlusion, so that balloon angioplasty, stenting, or other interventional procedures may then be performed to complete the treatment of the patient.

Figure 6:
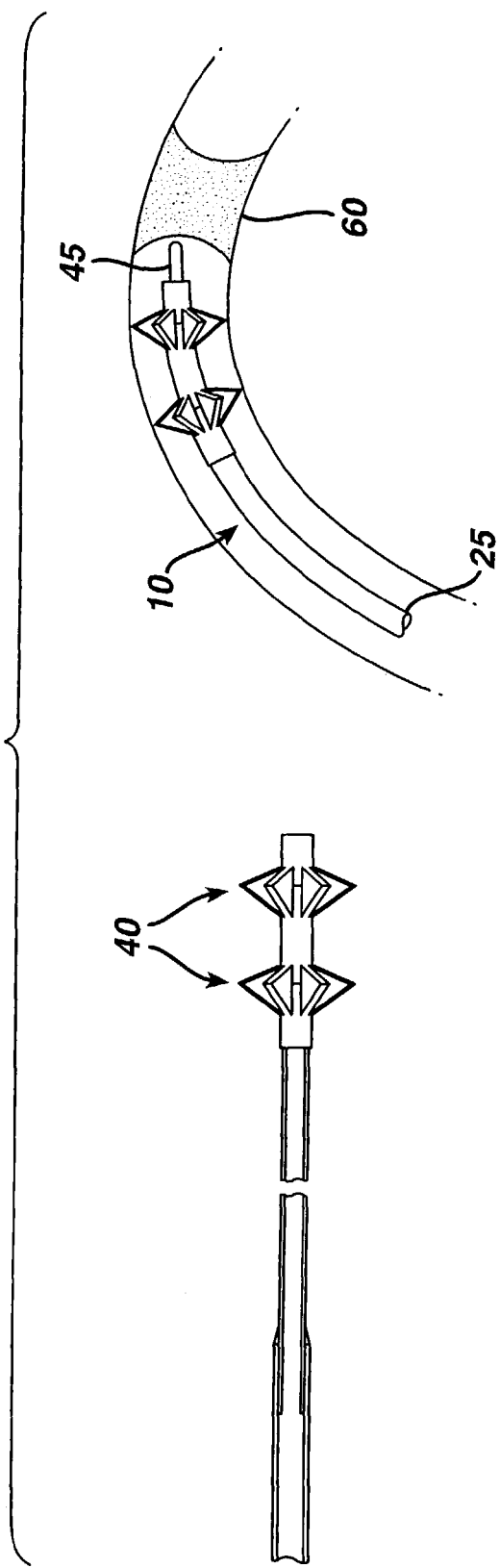
FIG. 6 is a simplified, partial, cross-sectional view of another exemplary embodiment of the total occlusion guidewire device, with multiple centering devices, in accordance with the present invention.

FIG. 6 illustrates a third exemplary embodiment of the total occlusion guidewire device. As illustrated in FIG. 6, a total occlusion guidewire device 10 may comprise two centering devices 40 attached to a flexible wire 25. As illustrated in FIG. 6, a boring guide tip 45 is attached to the rotatable core wire that has been inserted into the flexible wire 25. Centering devices may be joined by flexible members such as polymeric tubing or coils, to provide longitudinal flexibility and vessel configuration around bends. Centering devices may also be replaced with short, concentric balloons which may be pressurized simultaneously to center the device.

The total occlusion guidewire device 10 may be made from any number of suitable materials, and is preferably made from a superelastic alloy such as Nitinol.

The exemplary embodiment of the total occlusion guidewire device as illustrated in FIG. 6 functions in the same manner as the exemplary embodiment of the total occlusion guidewire device as illustrated in FIGS. 3, 4 and 5, and the centering devices 40 provide enhanced centering capability for the boring guide tip 45. As illustrated in FIG. 6, the boring guide tip 45 is substantially in contact with the chronic total occlusion 60. The boring guide tip 45 is rotated and advanced until the occlusion is fully opened. Once the occlusion is fully opened, additional interventional devices such as angioplasty balloons and stents may be advanced over the total occlusion guidewire device 10, and may be placed at the site of the occlusion 60, so that balloon angioplasty, stenting, or other interventional procedures may then be performed to complete the treatment of the patient.

Although shown and described are what are believed to be the preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A total occlusion guidewire configured for crossing a totally occluded vessel, said guidewire comprising:

a flexible wire having an outer diameter, an inner diameter, a proximal end and a distal end and a lumen extending therethrough;

a spreader comprising a structure having its longest length and its smallest diameter in a closed position and its shortest length and largest diameter in its expanded position and which is configured to expand and contract attached to the distal end of the flexible wire, the spreader comprising a plurality of first spiral longitudinally oriented struts having first and second ends, a plurality of second spiral longitudinally oriented struts having first and second ends, and a proximal end and a distal end, the first ends of the plurality of first longitudinally oriented struts being connected to the proximal end and the second ends of the plurality of first longitudinally oriented struts being connected to the first ends of the plurality of second longitudinally oriented struts such that it forms an articulation point for expansion and contraction of the spreader, and the second ends of the plurality of second longitudinally oriented struts being connected to the distal end, the first and second plurality of struts being configured to expand surrounding tissue, the plurality of first longitudinally oriented struts and the plurality of second longitudinally oriented struts being oriented in the same longitudinal direction; said spreader comprises a proximal portion and a distal portion, and a plurality of hingedly connected struts extending therebetween; and a core wire being slidably positioned within the lumen of the flexible wire for moving the spreader between the contracted and expanded states, the core wire being slidably moveable in a distal direction through the lumen of the flexible wire to make contact with the distal end of the spreader to move the spreader into a contracted state and slidably moveable in a proximal direction through the lumen of the flexible wire to make contact with the proximal end of the spreader to move the spreader into an expanded state.

2. The guidewire according to claim 1, wherein said flexible wire is made from super-elastic Nickel-Titanium alloy.

3. The guidewire according to claim 1, wherein said flexible wire incorporates segments made from a polymeric material.

4. The guidewire according to claim 1, wherein said spreader is made from super-elastic Nickel Titanium alloy.

5. The guidewire according to claim 1, wherein said flexible wire and said spreader are both made from super-elastic Nickel-Titanium alloy.

* * * * *